United States Patent [19]

Chen et al.

[11] Patent Number: 5,169,788
[45] Date of Patent: Dec. 8, 1992

[54] METHODS OF MEASURING MEMBRANE POTENTIAL USING J-AGGREGATE FORMING DYES

[75] Inventors: Lan B. Chen, Lexington; Glenn D. Steele, Jr., Swampscott, both of Mass.; Stephen T. Smiley, Stratford, Conn.

[73] Assignee: New England Deaconess Hospital Corporation, Boston, Mass.

[21] Appl. No.: 363,674

[22] Filed: Jun. 9, 1989

[51] Int. Cl.$^5$ .............................. C01N 21/76
[52] U.S. Cl. .................... 436/172; 435/29; 435/173; 435/968; 436/800
[58] Field of Search .............. 435/29, 173, 808, 820, 435/968; 436/800, 172

[56] References Cited

U.S. PATENT DOCUMENTS 4,343,782 8/1982 Shapiro ............................ 424/3
4,859,584 8/1989 Horan et al. ..................... 435/29

OTHER PUBLICATIONS

Jelley (1937) Nature, 139:631–632.
Draize et al. (1944) J. Pharmacol. Exptol. Therapy, 82:377–390.
Smith et al. (1972) Acta Cryst., B28:2793–2806.
Cohen et al. (1974) J. Membrane Biol., 19:1–36.
Hoffman et al. (1974) J. Physiol., 239:519–552.
Tedeschi (1974) Proc. Nat. Acad. Sci. USA, 71:583–585.
Sims et al. (1974) Biochemistry, 13:3315–3330.
Laris et al. (1975) Biochim. Biophys. Acta, 376:415–425.
Azzi (1975) Quart. Rev. Biophys., 8:237–316.
Doughty et al. (1976) Biochim. Biophys. Acta, 451:592–603.
Laris et al. (1976) Biochim. Biophys. Acta, 436:475–488.
Waggoner (1976) J. Membrane Biol., 27:317–334.
Hladky et al. (1976) J. Physiol., 263:287–319.
Bramhall et al. (1976) Biochem. Biophys. Res. Acta, 72:654–662.
Hada et al. (1977) Photograph. Sci. Eng., 21:83–91.
Ross et al. (1977) J. Membrane Biol., 33:141–183.
Tsien et al. (1978) J. Membrane Biol., 38:73–97.
Cohen et al. (1978) Rev. Physiol. Biochem. Pharmacol., 83:35–88.
Philo et al. (1978) Biochem. J., 174:801–810.
Deutsch et al. (1979) Proc. Natl. Acad. Sci. USA, 76:2175–2179.
Mitchell (1979) Science, 206:1148–1159.
Rottenberg (1979), Meth. Enzymol., LV:547–569.
Freedman et al. (1979) J. Gen. Physiol., 74:187–212.
Waggoner (1979) Meth. Enzymol., LV:689–695.
Summerhayes et al. (1982) Proc. Natl. Acad. Sci. USA, 79:5292–5296.
Waggoner (1979) Ann. Rev. Biophys. Bioeng., 8:47–68.
Bashford et al. (1979) Meth. Enzymol., LV:569–586.
Johnson et al. (1980) Proc. Natl. Acad. Sci. USA, 77:990–994.
Freedman et al. (1981) Inter. Rev. Cytol., (Suppl. 12), pp. 177–246.
Johnson et al. (1981) J. Cell. Biol., 88:526–535.
Johnson et al. (1982) Cell, 28:7–14.

(List continued on next page.)

Primary Examiner—Amelia Burgess Yarbrough
Attorney, Agent, or Firm—Lahive & Cockfield

[57] ABSTRACT

Disclosed is a method of detecting a localized biochemical event in a cell, wherein said event results in a change in the membrane potential of that cell. The method includes treating the cell with a composition containing a lipophilic, cationic dye having a delocalized positive charge and the ability to undergo multiple changes in fluorescence spectra upon aggregation. The cell is treated with the dye for a time sufficient to enable the dye to associate with the cell. Dye which has not associated with the cell is then removed. Fluorescence is observed when the cell is exposed to light having a wavelength suitable for exciting the dye. The spectrum obtained is indicative of the relative membrane potential of said cell, and a change in that membrane potential being indicative of the occurrence of a biochemical event.

20 Claims, 5 Drawing Sheets

OTHER PUBLICATIONS

Clark et al. (1982) Proc. Natl. Acad. Sci. USA, 79:1144–1148.
Clark et al. (1982) Nature, 295:605–607.
Terada et al. (1983) Cell Struct. Func., 8:161–170.
Kliot-Fields et al. (1983) Somatic Cell Genetics, 9:375–389.
Davis et al. (1985) J. Biol. Chem., 260:13844–13850.
Pena et al. (1984) Archives Biochem. Biophys., 231:217–225.
Singh et al. (1985) J. Biochem. Biophys. Meth., 11:95–108.
Tucker et al. (1986) Arch. Androl., 17:179–187.
Powers et al. (1986) J. Neurosurg., 64:918–923.
Chen (1988) Ann. Rev. Cell Biol., 4:155–181.

METHODS OF MEASURING MEMBRANE POTENTIAL USING J-AGGREGATE FORMING DYES

BACKGROUND OF THE INVENTION

This invention relates to the general health of a living cell, and to membrane potential as it relates to the general health and metabolic activity of a living cell. Specifically, this invention concerns methods of measuring and localizing relative changes in the membrane potential of a living cell, and relating such data to biochemical events occurring in the cell.

Qualitative measurements of gross changes in the health of a cell exposed to a suspected toxin have been made using techniques in the prior art such as the Draize test (Draize et al. (1945) Public Health Reports 60:377). In this in vivo test, a suspected toxin is placed in contact with the corneal tissues of the eye of a rabbit. Resulting injury and/or irritation resulting from the suspected toxin is then observed visually. However, besides being inhumane and expensive, this test measures the changes in multiple cells (corneal tissue) rather than a single cell, and test results are subjective, non-quantitative, and non-reproducible.

An alternative to this test is the in vitro occular toxicity test of Spilman et al. (The Toxicologist (1982) 2:A482) which monitors the effects of suspected toxins on cultured corneal cells instead of viable eyes. However, single cell measurements are not possible using this assay.

The general health of a cell can be reflected in its metabolic state. For example, a high level of respiration can be a good indication that the cell is functioning normally. A change in this rate may be indicative of the occurrence of a biochemical event in the cell, such as one resulting from an externally applied toxin or irritant.

Methods of measuring the average rate of respiration in multiple cells has been accomplished with the use of a Clark electrode. However, as in the Draize test, the metabolic state of a single cell cannot be determined by this method. Non-invasive methods such as NMR, appear promising, but do not, at present, have the necessary sensitivity to enable such a measurement.

Viability measurements do enable the examination of single cells. Vital staining, for example is routinely used as measure of cell viability. In this assay, live cells readily incorporate certain dyes which are not taken up by dead cells. Dye exclusion measurements are essentially similar to vital staining, except that it is the dead cells which show a preferential ability to incorporate the dye. However, such gross measurements are not indicative of the health or metabolic state of a particular cell per se. Moreover, there are no accurate methods for assessing the health of a single living cell.

The plasma and mitochondrial membranes of living cells are known to be characterized by specific transmembrane potentials. In the case of mitochondria, a proton gradient exists across the inner membrane as the result of proton pumping by the respiratory chain located in this membrane. Mitochondrial membrane potential is not constant over time; many naturally occurring intracellular biochemical events routinely change the membrane potential. For example, the mitochondrial membrane potential is known to drive the synthesis of ATP, and in doing so, the potential changes or even becomes dissipated. The presence of irritants and injury to the cell also affect membrane potential.

The fluorescence and absorption characteristics of certain cationic dyes (e.g., cyanines, rhodamines, thiapyryliums, pyryliums) are known to be sensitive to membrane potential. The cyanine dyes, for example, demonstrate fluorescence and absorption changes as large as 80 when cells become negatively charged inside (hyperpolarized). Generally, this sensitivity of cyanine yes to membrane potential depends on the permeant nature of these cationic molecules. The distribution of these dyes between the cell interior and the medium is driven by the membrane potential (Chen (1988) Ann. Rev. Cell Biolol. 4:155-181), with the cationic dye being accumulated in cells when the cells become hyperpolarized.

Most accumulated cyanine dyes either (1) form aggregates that are nonfluorescent and absorb at a different wavelength then when outside a cell, (2) bind to the cell contents and the inner side of the membrane forming complexes that absorb or fluoresce at different intensities then when outside a cell, or (3) exhibit fluorescence quenching with little concomitant change in absorption. The particular mode of the optical change depends on the dye structure, the cell system being studied, and the experimental conditions.

Approaches to measuring the metabolic state of a single cell which involve the use of fluorescent dyes are promising in view of the predicted sensitivity (i.e., the ability to monitor single cells), the existence of more than 100,000 fluorescent dyes, the rapid development of hardware, the exquisite susceptibility of emission spectrum to environments, and the possibility of using non-invasive techniques. In fact, the energized state of mitochondria in vitro has been monitored using exogenous fluorescent dyes such as 1-anilino8-naphthalene sulfonate (ANS) and Oxonol V (Bashford et al. (1979) Meth. Enzymol. 55:569-586). Unfortunately, these dyes are not very membrane permeable, and thus their use has been limited to isolated mitochondria.

Other fluorescent dyes such as rhodamine 123 and various cyanines have been used to measure membrane potential. These dyes are able to penetrate the plasma and mitochondrial membranes of living cells where they fluoresce in a single spectral range or are quenched. In order to measure a cell's metabolic activity, such dyes have been used to label mitochondria, the organelles responsible for the respiratory functions and energy production in the cell; the degree to which mitochondria are present in a cell is directly proportional to the cell's metabolic activity.

Cyanine dyes in an aqueous solution may exist as three distinct molecular species: monomers; H-aggregates; and J-aggregates. Each species may be characterized by its unique absorption/fluorescence spectrum. The spectrum of a monomer usually consists of a broad peak with a vibrational shoulder at the shorter wavelength side. This peak has been called the M-band (for monomer). Dye aggregation may lead to a shift of the absorption maximum to a shorter wavelength (called H-aggregates or H-bands, for hypsochromic), or to a longer wavelength (called J-aggregates or J-bands for its discoverer, Jelly) (Jelly (1937) Nature 139:631-632). H-aggregates do not fluoresce, and this feature has been previously exploited for the measurement of membrane potentials (Cohen and Salzberg (1978) Rev. Physiol. Biochem. Pharmacol. 83:35-88: Bashford and Smith (1979) Meth. Enzymol. 55:569-586; Waggoner (1979)

Ann. Rev. Biophys. Bioeng. 8:47-68; and Freedman (1981) Inter. Rev. Cytolo. 12:177-246). In contrast, J-aggregates are often intensely fluorescent. The wavelength of such fluorescence is very similar to the absorption wavelength of the J-aggregates. This lack of a Stoke's shift is termed "resonance fluorescence."

The rhodamine and the cyanine dyes used to date to measure respiration have failed to reveal any heterogeneity in fluorescent intensity among mitochondria within a single cell (see e.g., Johnson et al. (1981) J. Cell Biol. 88:526-535; and Cell (1982) 28:7-14). The human eye, photography, and video imaging all have limited ranges for a linear response to increasing light intensity. Consequently, once the fluorescent intensity reaches a certain level, prior art detection systems fail to respond to further increases in fluorescence. Mitochondria with higher potentials in the same cell are therefore difficult to distinguish from those with lower potentials because they are already brightly stained.

Furthermore, most previously used cyanines form H-aggregates rather than J-aggregates. As discussed above, H-aggregates quench the dye fluorescence. Thus, an increase in dye uptake as a result of higher mitochondrial membrane potential may not necessarily lead to brighter fluorescence; it may reduce the fluorescence to an extent that such mitochondria become undetectable.

Accordingly, it is an object of the present invention to provide a method of monitoring the general health of a single living cell.

Another object is to provide a method of measuring the respiratory state of a single cell, the state being indicative of the general health of the cell.

Yet another object is to provide a method of measuring the relative membrane potential in a living cell.

Still another object is to provide a method of monitoring the occurrence of a biochemical event in a cell.

Another object is to provide a method of determining to what extent a substance, to which a cell is exposed, poses a health risk to that cell.

SUMMARY OF THE INVENTION

The present invention provides methods of determining the relative mitochondrial membrane potential of a living cell. These methods include treating the cell with a composition comprising a lipophilic, cationic dye for a time sufficient to enable the dye to associate with the cell. This dye has a delocalized positive charge and the ability to undergo multiple changes in fluorescence spectra upon aggregation. In a preferred embodiments of the invention, 5,5',6,6'-tetrachloro-1,1',3,3'-tetraethylbenzimidazolocarbocyanines such as bromide, chloride, iodide, and sulfonate salts of 5,5',6,6'-tetrachloro-1,1',3,3'-tetraethylbenzimidazolocarbocyanines are used.

Following the treating of the cell, any dye which has not associated with the cell is then removed. The treated cell is exposed to light having a wavelength suitable for exciting the dye, so that the excited dye emits light having a wavelength different from the exciting light, or fluorescence. The fluorescence spectra, which is indicative of the relative membrane potential of the cell, is then determined.

In one embodiment of the invention, detection of the fluorescence is accomplished with an epifluorescence microscope, while in other embodiments, a fluorescence spectrophotometer or a flow cytometer are used.

This method can also be employed to detect a localized biochemical event in a living cell, wherein that event results in a change in the membrane potential of the cell. The spatial location of the biochemical event can be localized by identifying the location of fluorescence change in a particular part of the membrane. In one embodiment, an epifluorescence microscope is used to localize the fluorescence, while in an alternative embodiment, a fluorescence spectrophotometer is used.

BRIEF DESCRIPTION OF THE DRAWINGS

The foregoing and other objects of the invention, the various features thereof, as well as the invention itself, may be more fully understood from the following description, when read together with the accompanying drawing in which.

DESCRIPTION OF THE INVENTION 5,5',6,6'-tetrachloro-1,1',3,3'-tetraethylbenzimidazolocarbocyanines are lipophilic permeants with a delocalized positive charge. More specifically, bromide, iodide, chloride, and sulfonate salts of this cyanine are particularly useful in practicing the present invention. The molecular structure of one such cyanine, JC-1 is shown in FIG. 1A. JC-1 has been extensively used and studied as a sensitizer for silver halide-based photographic emulsion.

Figure 1:
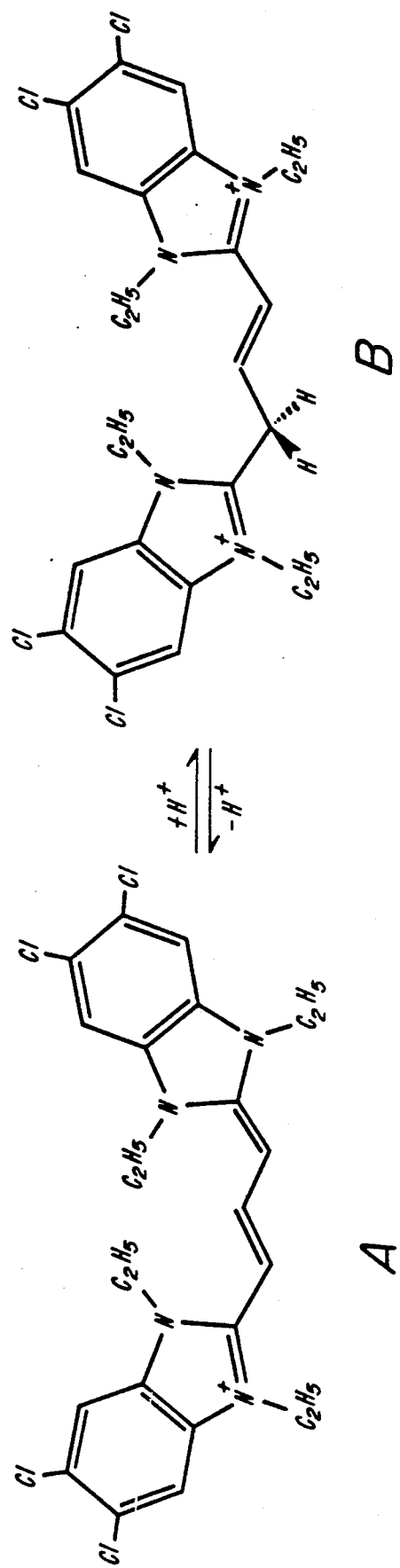
FIG. 1 shows the molecular structure of 5,5',6,6'-tetrachloro-1,1',3,3'-tetraethylbenzimidazolocarbocyanine iodide (JC-1)

Like most cyanine dyes, JC-1 in aqueous solution may exist as three distinct molecular species: monomers; H-aggregates; and J-aggregates. The extent to which each species is present is governed by two distinct and reversible equilibria. One of these equilibria is governed by pH. For example, the apparent pKa of JC-1 is known to be 7.9. Above pH 7.9, the majority of JC-1 molecules have a single delocalized positive charge. One resonance form is shown in FIG. 1. Other resonance forms may be drawn in which the double bonds are shifted such that the positive charge falls on one of the other four nitrogen atoms. The conjugated electron system allows this species of JC-1 to absorb energy corresponding to visible blue-green wavelengths. Subsequent release of the absorbed energy results in the emission of green light.

Below pH 7.9, most of the JC-1 molecules are protonated as shown in FIG. 1B. Nuclear magnetic resonance studies have confirmed that the molecules are protonated at a carbon of the methine chain adjacent to the heterocyclic nuclei. Thus, JC-1 and other cyanines are carbon acids rather than the more common nitrogen acids.

Protonation at this position has two major consequences. First, the molecule now has an overall charge of +2. Second, the conjugated methine chain has been disrupted, resulting in the loss of absorbance and fluorescence of visible light. Unlike thia-, indo-, oxa-, or classic cyanines, the positive charges on the carbon acids of imidazolocyanines like JC-1 remain delocalized (i.e., resonance forms can still be drawn which place the positive charges on either nitrogen of each heterocyclic nucleus). Thus, these molecules remain lipophilic in their acid form.

Figure 2B:
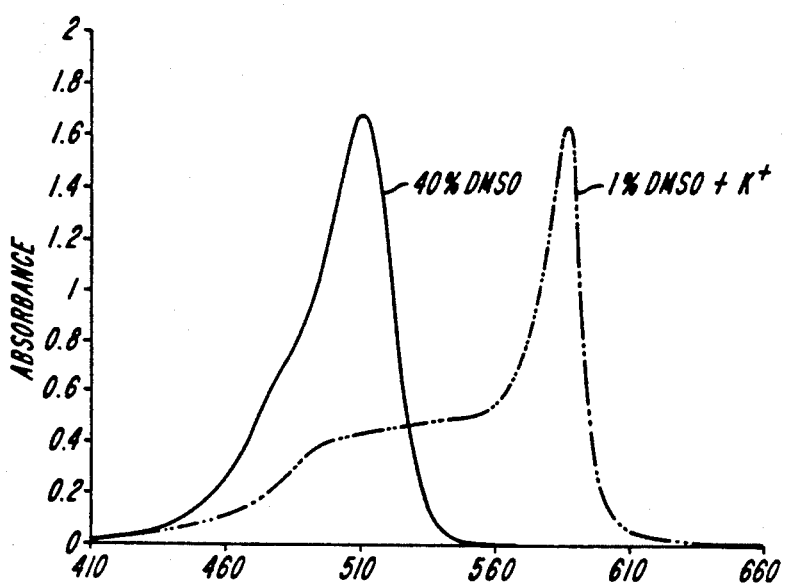
FIG. 2 is a graphic representation of the effect of pH (A), ionic strength (B), and concentration (C), on the absorbance and fluorescence spectra of JC-1 in solution.
Figure 2C:
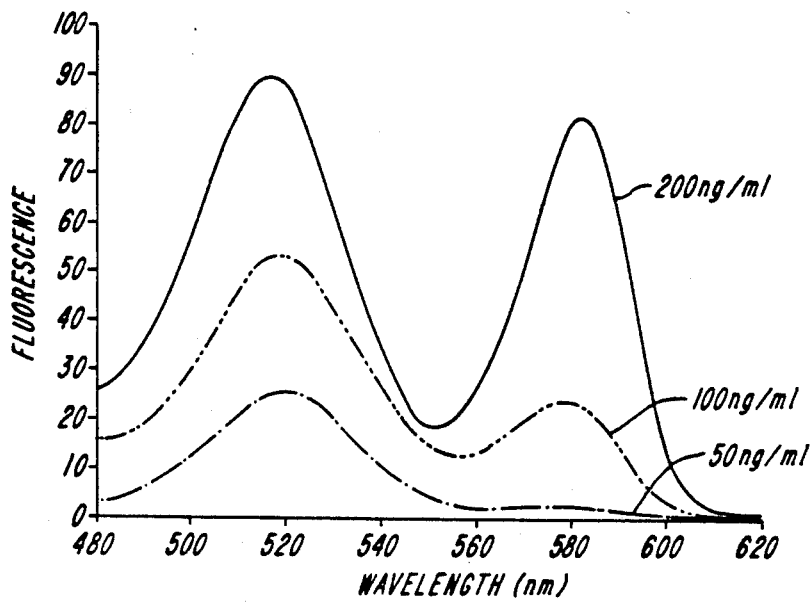
Figure 2A:
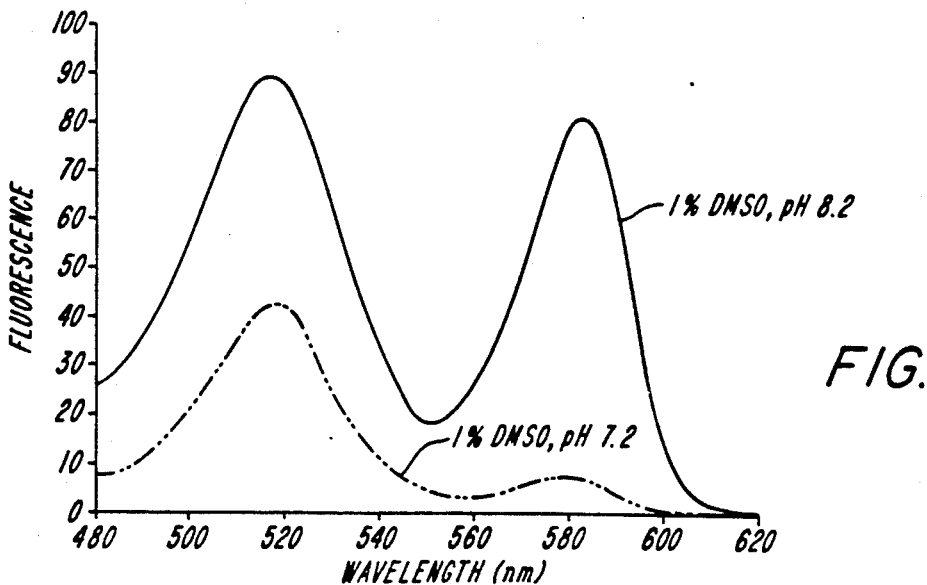

FIG. 2A shows the fluorescence spectra of JC-1 at pH 8.2 (solid line) and pH 7.2 (dashed line) in 50 mM Tris-HCl containing 1% DMSO. As shown, J-aggregate formation is strongly favored by pH 8.2, the intramitochondrial pH.

A second equilibrium exists between monomers and aggregates consisting of dimers, trimers, or higher polymers. Factors such as ionic strength, dye concentration, temperature, and the presence or absence of organic deaggregants and organic solvents effect this equilibrium. For example, FIG. 2B shows representative absorbance spectra resulting from different ionic conditions. The first peak (absorption maximum=510 nm and fluorescence maximum =520 nm) is the monomeric dye species, and second peak (absorption maximum=585 nm and fluorescence maximum=585 nm) is the J-aggregate (Hada et al., 1977; Smith and Luss, 1972). The solid line is in 40% dimethyl sulfoxide (DMSO) in double distilled water at pH 7.2; the dashed line is 1% DMSO in high $K^+$ buffer. As shown, J-aggregate formation is favored by a buffer with ionic strength comparable to that inside the cells.

FIG. 2C shows the fluorescence spectra of JC-1 at various concentrations in 50 mM Tris-HCl, pH 8.2 containing 1% DMSO. The solid line is 200 ng/ml; the dashed line is 100 ng/ml; and the dotted line is 50 ng/ml. As shown, J-aggregate formation is highly concentration dependent.

These findings demonstrate that conditions favoring J-aggregation formation in aqueous environments include high ionic strength comparable to that found intracellularly, increased dye concentration, and higher PH. In addition, these findings indicate that the intramitochondrial environment should permit the formation of J-aggregates of JC-1.

Figure 3A:
FIGS. 3A-3C are photographic representations showing the fluorescence of JC-1 taken up by human breast carcinoma MCF-7 cells and excited under green light (FIG. 3A), blue light (FIG. 3B), and light blue light (FIG. 3C)
Figure 3B:
Figure 3C:
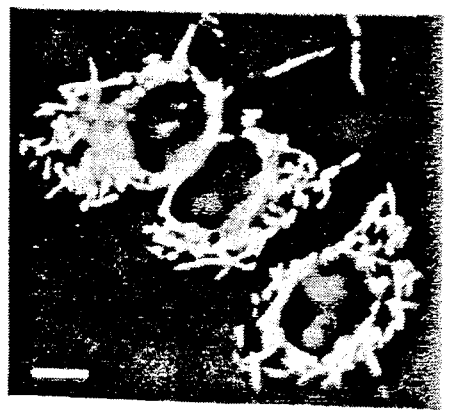

That living cells can take up JC-1, and that JC-1 can fluoresces metachromasically is illustrated in FIG. 3. When cultured human breast carcinoma MCF-7 cells stained with JC-1 were examined by standard epifluorescence microscopy, visualization under green excitation with a narrow band pass filter produced red fluorescence (FIG. 3A); under blue excitation with a narrow band pass filter produced green fluorescence (FIG. 3B); and under light-blue excitation with a longpass filter produced orange fluorescence (FIG. 3C). Although most mitochondria shown in FIG. 3C display orange fluorescence, there are also a few mitochondria with only green fluorescence. Orange regions indicate the presence of both green and red fluorescence, whereas green regions have no red fluorescence.

Figure 4A:
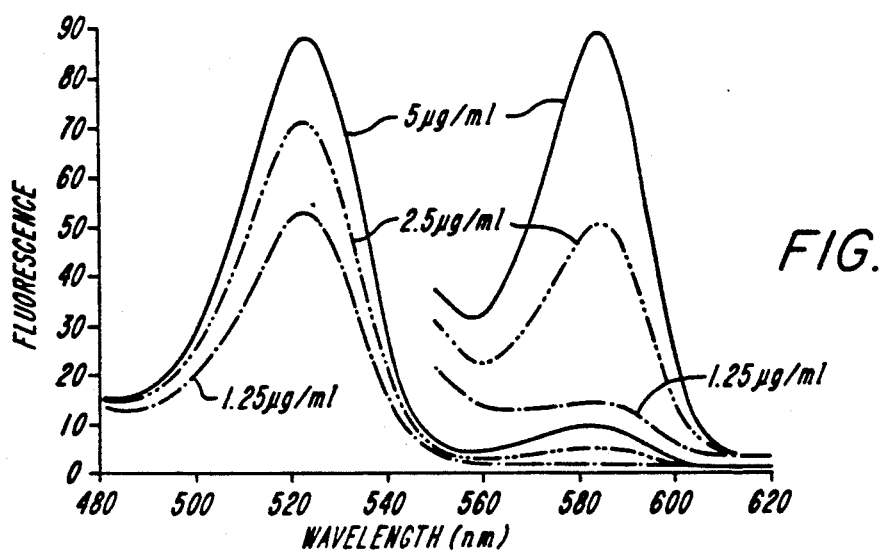
FIG. 4 is a graphic representation of the effect of (A) and (B), concentration, and (C), mitochondrial membrane depolarization on the uptake and fluorescence of JC-1 by CX-1 cells.

To establish that in living cells, green fluorescence represents the monomer and the red fluorescence represents the J-aggregate, human colon carcinoma CX-1 cells were incubated with different concentrations of JC-1, trypsinized, transferred to a cuvette, and analyzed by fluorescence spectrophotometry. FIG. 4A shows the fluorescence spectrum, obtained. The two peaks, at 520 nm and 585 nm correspond to the monomer fluorescence and the J-aggregate fluorescence, respectively (as demonstrated in FIG. 2). Thus, in living cells, the green fluorescence represents the monomer, and the red fluorescence the J-aggregate.

The results shown in FIG. 4A also confirm that J-aggregate formation is critically dependent on the concentration of JC-1 attained by mitochondria. CX-1 cells incubated with JC-1 at 1.25 $\mu$g/ml results in the formation of a very small amount of J-aggregate was observed; at 2.5 $\mu$g/ml, more was generated; at 5 $\mu$g/ml., the amount of J-aggregate greatly increased.

Effects of temperature and time on the uptake of JC-1 by living cells and J-aggregate formation therein were also investigated. No J-aggregate (no red fluorescence) was detected when MCF-7 cells were incubated at 4°C. with JC-1; a small amount was detected at 25°C.; and a large amount was detected at 37°C. The cells were then mounted in a live cell chamber containing 10 $\mu$g/ml of JC-1 in culture medium and maintained at 37°C. on a microscope stage with an air curtain. The uptake of JC-1 and formation of J-aggregates were monitored at 1 minute intervals by fluorescence microscopy: after 3 min., green fluorescence with a few speckles of red fluorescence was detected in mitochondria: at 5 min., the intensity of green fluorescence significantly increased, and rod-like structures with red fluorescence were detected; at 7 min., almost every mitochondrion exhibited red fluorescence; and after 10 min., all mitochondria were intensely illuminated with red fluorescence. Taken together, these results indicate J-aggregate formation is favored by higher temperatures and greater incubation times.

Figure 4B:
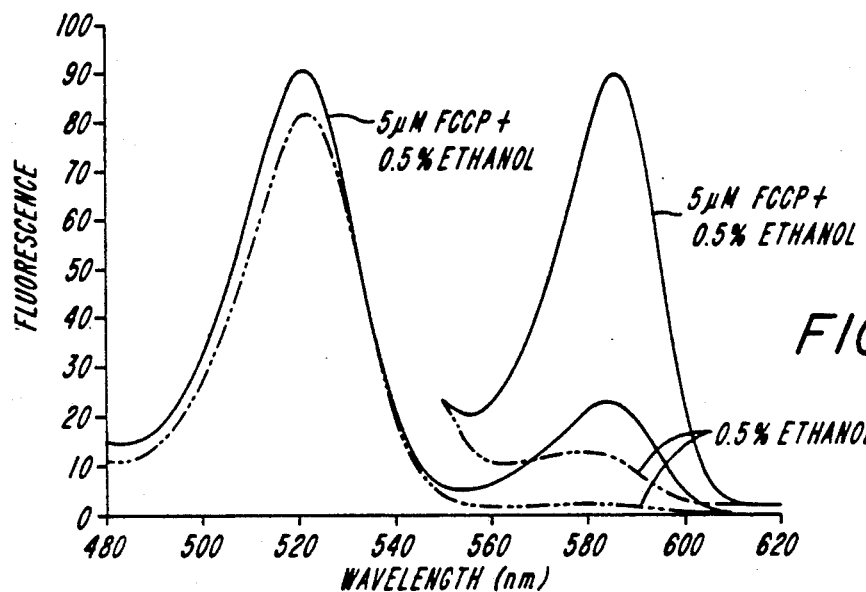
Figure 4C:
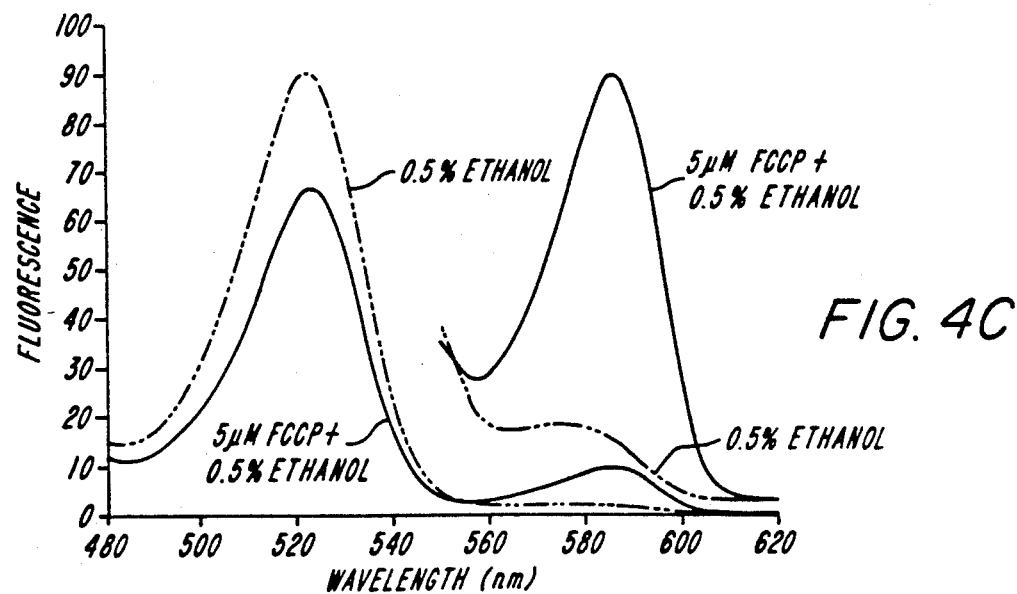

The uptake of lipophilic permeants (such as JC-1) with a delocalized positive charge is expected to be driven by membrane potential. To extend such an expectation to J-aggregate-forming dyes, the effects of a variety of drugs and ionophores were tested. FIG. 4B shows that in the presence of FCCP, a proton ionophore that abolishes the electrochemical gradient, very little J-aggregate was detected. These results suggest that the formation of J-aggregates is dependent on the presence of an electrochemical gradient. When cells were allowed to form J-aggregates, and then placed in medium containing FCCP, the J-aggregates rapidly disappeared (FIG. 4C). Therefore, the maintenance of J-aggregates in mitochondria is also dependent upon an electrochemical gradient. Other agents known to abolish the mitochondrial electrochemical gradient (including FCCP, dinitrophenol, azide plus oligomycin, antimycin A plus oligomycin, and rotenone plus oligomycin) not only prevented the formation of J-aggregates but also disintegrated preformed J-aggregates.

To identify the component of the electrochemical gradient that is responsible for the formation and maintenance of J-aggregates, the effects of two ionophores were investigated: valinomycin, a $K+$ ionophore that dissipates the membrane potential but not the pH gradient, and nigericin, a $K+/H+$ ionophore that abolishes the pH gradient but induces a compensatory increase in membrane potential with continued respiration. FIG.

5B shows that nigericin in the presence of ouabain to inhibit hyperpolarization of the plasma membrane) dramatically increases the formation of J-aggregates in CCL22 bovine kidney epithelial cells such that every mitochondrion had a detectable amount of J-aggregate in comparison with untreated controls. On the other hand, valinomycin substantially prevented the uptake of JC-1 and J-aggregate formation. When cells were prestained with JC-1 and placed in valinomycin or nigericin in the absence of dye, the former abolished the orange fluorescence and the latter had no observable effect.

These results indicate that the pH gradient is not required either for the uptake of JC-1 and subsequent formation of J-aggregates or for the maintenance of preformed J-aggregates. The component of the electrochemical gradient responsible for the formation and maintenance of J-aggregates in mitochondria is thus the membrane potential.

Figure 5A:
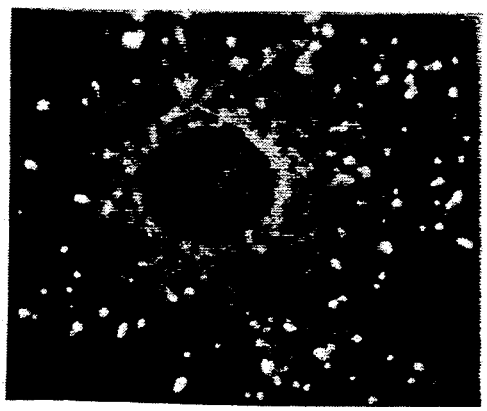
FIGS. 5A and 5B are photographic representations of the epifluorescence localization of JC-1 in (FIG. 5A) untreated control CCL22 bovine kidney cells in high K+buffer, and (FIG. 5B) cells treated with nigerin and ouabain in high K+buffer.

In living cells, mitochondria are surrounded by the plasma membrane whose potential has a pre-concentration effect on the mitochondrial accumulation of lipophilic cations (Davis et al., 1984). If J-aggregate formation is largely membrane potential dependent, a reduction in the plasma membrane potential should also lead to a reduction in J-aggregate formation. Indeed, the green fluorescence shown in FIG. 5A indicates that incubating CX-1 cells in high $K^+$ buffer dissipates the plasma membrane potential, thereby reducing formation of J-aggregate.

Figure 6:
FIG. 6 is a photographic representation of the epifluorescence localization of JC-1 monomers and J-aggregates in the human foreskin fibroblast cell line, FS-2.

To determine if JC-1 is taken up equally and similarly by different cells, a variety of cell types and cell lines were treated with JC-1 at 10 μg/ml in culture medium for 10 minutes. In many of these cells, mitochondria were observed with simultaneous red fluorescence and green fluorescence in different regions. FIG. 6 shows such mitochondria in normal human foreskin fibroblasts.

The two equilibria discussed above may both be relevant to the formation of red and green mitochondria. When JC-1 is diluted from a stock solution into physiological buffer of pH 7.2, much of the JC-1 should exist as the uncolored, doubly positively charged carbon acid (the apparent pKa of the dye is 7.9). This species of JC-1 should be taken up by the cells in response to their Nernst potentials, since the molecule is a delocalized lipophilic cation. Once inside the mitochondria, however, this species of JC-1 will revert back to its basic, monomeric form and fluoresce green because the intramitochondrial pH is known to be 8.2. However, with continuous uptake of JC-1, J-aggregates will eventually form when the concentration of monomer reaches nadir.

The invention will be further understood from the following nonlimiting examples.

EXAMPLES

1. Cell Culture

"Normal" African green monkey kidney cell line CV-1 obtained from American Type Culture Collection (ATCC), (Rockville, MD), normal human fibroblast strain FS-2 (obtained from Dr. R. Sager (Dana-Farber Cancer Institute, Boston, MA), and human breast carcinoma cell line MCF-7 (obtained from Michigan Cancer Foundation, Detroit, MI) were grown in Dulbecco's modified Eagles' medium (GIBCO, Rockville, MD) supplemented with 10% calf serum (M.A. Bioproducts, Rockville, MD). Human colon carcinoma cell line CX-1 (obtained from Dr. S. Bernal, (Dana-Farber Cancer Institute, Boston, MA) were grown in 50% Dulbecco modified Eagles' medium and 50% RPMI 1640 medium (GIBCO) supplemented with 5% calf serum and 5% NuSerum (Collaborative Research, Lexington, MA). Bovine kidney epithelial cell line CCL22 (obtained from the ATCC); and normal mouse bladder epithelial cells (prepared essentially by the procedures of Summerhayes and Franks (1979) Proc. Natl. Acad. Sci. (USA) 79:5292-5296, herein incorporated by reference), were grown in F12 medium (GIBCO) supplemented with 10% fetal bovine serum (GIBCO). All cells were maintained at 37° C., 5% $CO_2$ and 100% humidity.

2. Staining of Cells for Microscopy

All cells were grown on 12 mm square glass coverslips (Bradford Scientific, Epping, NH), and stained with 50 μl of 10 μg/ml JC-1 (Polaroid Co., Cambridge, MA) in Dulbecco's modified Eagles' medium for 10 minutes in a cell culture incubator. Cells were rinsed in dye-free culture medium and mounted in a living cell chamber made of 0.7 mm thick silicon rubber (N.A. Reiss, Belle Mead, NJ) essentially as described by Johnson et al. ((1980) Proc. Natl. Acad. Sci. (USA) 77:990-994), herein incorporated as reference.

3. Fluorescence Microscopy

A Zeiss Axiophot Microscope (Woburn, MA) or a Zeiss Photomicroscope III equipped with epifluorescence optic was used to monitor fluorescence. Objective lenses used included Planapo 40X (N.A. 1.3), Planapo or Neofluar 100X (N.A. 1.2). A 100 W mercury bulb was used for either microscope. Microscopic images were recorded on Kodak Professional Ektamatic P800/1600 positive films at E.I. 800 and developed by E-6 process at Push 1. Color photographs were made with Ilford Cibachrome A-II papers developed by a Cibachrome automatic processor.

4. Spectrophotometric Analysis

A. JC-1 (10 μg/ml) in 40% dimethyl sulfoxide (DMSO) in double distilled water, PH 7.2, or in 1% DMSO in high $K^+$ buffer (3.6 mM NaCl, 137 mM KCl, 0.5 mM $MgCl_2$, 1.8 mM $CaCl_2$, 4 mM Hepes, 1 mg/ml dextrose, and 1% modified Eagles' medium amino acid solution [100X, GIBCO], PH 7.2) was placed in a 1 cm quartz cuvette and examined by a Beckman DU-70 spectrophotometer (San Diego, CA). The results are shown in FIG. 2A.

B. JC-1 at various concentrations (200 ng/ml; 100 ng/ml; and 50 ng/ml) was dissolved in 50 mM Tris-HCl, pH 8.2 containing 1% DMSO, mixed thoroughly for 10 minutes in a 1 cm quartz cuvette equipped with a magnetic stirrer, and examined as described in (A). The results are shown in FIG. 2B.

C. 200 ng/ml JC-1 was dissolved in 50 mM Tris-HCl containing 1% DMSO at pH 8.2 or pH 7.2.

D. Human breast carcinoma MCF-7 cells were stained with 10 g/ml JC-1 in culture media at 37° C. for 10 min. They were then examined by epifluorescence microscopy under green excitation, blue excitation with short pass filter, and light blue excitation under a filter that allows both red fluorescence from J-aggregate and green fluorescence from monomer to be detected simultaneously. The results are shown in FIG. 3.

E. CX-1 cells in culture medium were incubated with JC-1 at 1.25 ug/ml, 2.5 ug/ml, and 5 ug/ml. The results are shown in FIG. 4A.

F. Procedures were the same as in (E) except the JC-1 (10 μg/ml)-containing buffer was supplemented with 5 μM trifluoromethoxyphenyl hydrazone (FCCP) and 0.5% ethanol, or 0.5% ethanol. The results are shown in FIG. 4B.

G. Procedures were the same as in (E). After 10–20 minutes of incubation, the cells were then placed in cell medium containing 5 μM FCCP and 0.5% ethanol, or 0.5% ethanol, alone. The results are shown in FIG. 4C.

H. Human colon carcinoma cell line CX-1 in 60 mm culture dishes were grown to 50% confluence in 50% Dulbecco modified Eagles' medium and 50% RPMI 1640 medium supplemented with 5% calf serum (M.A. Bioproducts, (Rockville, MD) and 5% Nuserum (Collaborative Research, Lexington, MA) at 37 C. and 5% $CO_2$. The cells were washed with (5 ml) and incubated in (1 ml) low K+buffer (137 mM NaCl, 3.6 mM KCl, 0.5 mM $MgCl_2$, 1.8 mM $CaCl_2$, 4 mM Hepes, 1 mg/ml dextrose, and 1% modified Eagles' medium amino acid solution [100X, GIBCO], pH 7.2) for 10 minutes. Cells were then washed three times with (2 ml each) and left in (1 ml) trypsin (1X, M.A. Bioproducts) in low K+buffer for 5 minutes. About 0.8 ml of cell suspension was mixed with 1.2 ml of low K+buffer in a 1 cm quartz cuvette for 5 minutes. Recordings of spectra from 550 to 620 nm were repeated at a higher detector sensitivity. The results are shown in FIG. 4A.

Figure 5B:
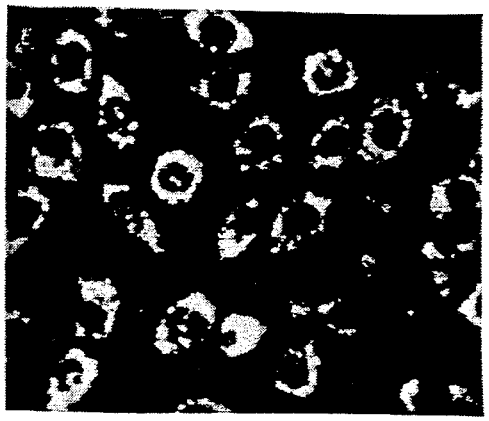

Fluorescent spectra were made as described in FIG. 3. Recordings of spectra from 550 to 620 nm were repeated at a higher detector sensitivity. The results are shown in FIG. 5 wherein JC-1 at 5 μg/ml in low K+buffer is solid curve, and 2.5 μg/ml is the dotted curve.

The invention may be embodied in other specific forms without departing from the spirit or essential characteristics thereof. For example, a combination of lipophilic, cationic dyes may be equally as effective in the method of the present invention. The present embodiments are therefore considered to be in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method of detecting a localized biochemical event in a cell, wherein said event results in a change in the membrane potential of said cell, said method comprising the steps of:
   (a) treating said cell with a composition comprising a lipophilic, cationic dye for a time sufficient to enable said dye to associate with said cell, said dye having a delocalized positive charge and being characterized by a fluorescence spectrum having a peak substantially at a first wavelength when in monomer form and a fluorescence spectrum having a peak substantially at a second wavelength when in aggregated form;
   (b) removing said dye which has not associated with said cell;
   (c) exposing said cell to light having a wavelength suitable for exciting fluorescence by said associated dye, whereby said excited dye emits light having a wavelength different from said exciting light; and
   (d) determining the spectrum of said emitted light, said determined spectrum being indicative of the relative membrane potential of said cell, and a change in said membrane potential being indicative of the occurrence of a biochemical event.

2. The method of claim 1 wherein said treating step comprises treating said cell with a salt of the lipophilic dye, 5,5',6,6'-tetrachloro-1,1',3,3'-tetraethylbenzimidazolocarbocyanine iodide.

3. The method of claim 2 wherein said salt is selected from the group consisting of chloride, bromide, iodide, and sulfonate.

4. The method of claim 1 further comprising the step of identifying the spatial location of said fluorescence within said cell, said location of said fluorescence being indicative of the location of said biochemical event.

5. The method of claim 1 wherein said exposing and determining steps comprise the use of an epifluorescence microscope.

6. The method of claim 4 wherein said exposing and determining steps comprise the use of an epifluorescence microscope.

7. The method of claim 1 wherein said exposing and determining steps comprise the use of a fluorescence spectrophotometer.

8. The method of claim 1 wherein said determining step comprise the use of a flow cytometer.

9. The method of claim 4 wherein said exposing and determining steps comprise the use of a fluorescence spectrophotometer.

10. The method of claim 4 wherein said determining step comprise the use of a flow cytometer.

11. A method of determining the relative membrane potential of a living cell comprising the steps of:
    (a) treating said cell with a composition comprising a lipophilic, cationic dye for a time sufficient to enable said dye to associate with said cell, said dye having a delocalized positive charge and being characterized by a fluorescence spectrum having a peak substantially at a first wavelength when in monomer form and a fluorescence spectrum having a peak substantially at a second wavelength when in aggregated form;
    (b) removing said dye which has not associated with said cell;
    (c) exposing said cell to light having a wavelength suitable for exciting fluorescence by said associated dye, whereby said excited dye emits light having a wavelength different from the exciting light; and
    (d) determining the spectrum of said emitted light, said determined spectra being indicative of the relative membrane potential of said cell.

12. The method of claim 11 wherein said treating step comprises treating said cell with a salt of the lipophilic dye, 5,5',6,6'-tetrachloro-1,1',3,3'-tetraethylbenzimidazolocarbocyanine.

13. The method of claim 12 wherein said salt is selected from the group consisting of chloride, bromide, iodide, and sulfonate.

14. The method of claim 11 further comprising the step of identifying the spatial location of said fluorescence within said cell, said location of said fluorescence being indicative of an area of membrane at which said membrane potential was determined.

15. The method of claim 11 wherein said exposing and determining steps comprise the use of an epifluorescence microscope.

16. The method of claim 14 wherein said exposing, determining, and identifying steps comprise the use of an epifluorescence microscope.

17. The method of claim 11 wherein said exposing and determining steps comprise the use of a fluorescence spectrophotometer.

18. The method of claim 14 wherein said exposing and determining steps comprise the use of a fluorescence spectrophotometer.

19. The method of claim 11 wherein said exposing and determining steps comprise the use of a flow cytometer.

20. The method of claim 14 wherein said exposing and determining steps comprise the use of a flow cytometer.

* * * * *